United States Patent [19]

Nalewajek et al.

[11] Patent Number: 4,633,005

[45] Date of Patent: Dec. 30, 1986

[54] METHOD FOR THE PREPARATION OF ALLYL PHOSPHONATE DIESTERS

[75] Inventors: David Nalewajek, West Seneca; David S. Soriano, Cheektowaga, both of N.Y.

[73] Assignee: Allied Corporation, Morris Township, Morris County, N.J.

[21] Appl. No.: 627,141

[22] Filed: Jul. 2, 1984

[51] Int. Cl.$^4$ .............................................. C07F 9/40
[52] U.S. Cl. ................................................... 558/125
[58] Field of Search ......................... 260/969; 558/125

[56] References Cited

U.S. PATENT DOCUMENTS 3,925,515  12/1975  Velker et al. ..................... 260/969
4,017,564   4/1977  Arend et al. ..................... 260/969

Primary Examiner—Anton H. Sutto
Attorney, Agent, or Firm—Jay P. Friedenson; Patrick L. Henry

[57] ABSTRACT

Allylphosphonate diesters are prepared by reacting an appropriate allyl halide or alcohol with an appropriate phosphite compound in the presence of a catalytically effective amount of a phosphinated $d^8$ transition metal catalyst.

19 Claims, No Drawings

METHOD FOR THE PREPARATION OF ALLYL PHOSPHONATE DIESTERS

BACKGROUND OF THE INVENTION

1. Field of the Invention

This invention relates to an improved process for preparing allylic pentavalent organophosphorus compounds. More particularly, this invention relates to a process of preparing allylic pentavalent organophosphorus diester compounds by reacting the corresponding allyl halide with an appropriate phosphite ester compound in the presence of a pentakis (phosphite) complex of a $d^8$ transition metal.

2. Prior Art

Esters of vinyl phosphonic acid serve as useful reactants in a large number of reactions to form compounds which are useful in agriculture. The versatility of this intermediate material results from reactivity of the vinylic group toward nucleophilic compounds. By manipulations of this reactivity via reaction with nucleophilic compounds such as alcohols, thiols, amines, nitroalkanes, active methylene compounds and the like, a wide class of agricultural chemicals can be prepared. For example, esters of vinylphosphonic acid compounds can be reacted with phosgene or oxalyl chloride to prepare plant growth regulants as described in detail in German Offen No. 2,153,149 (1983). Similarly, such esters can be reacted with amines in accordance with the procedures of Bartlett, et al., Tet Letters 24:2937 (1973) to prepare phosphatase inhibitors.

Furthermore, esters of vinyl-phosphonic acid can be used as precursors in the preparation of compounds which can be used in fields other than agriculture. For example, these compounds can be used in the preparation of heat and light stabilizers for polymers as well as flame retardant or shrinkage retardant additives for polymers. Such uses are described in detail in U.S. Pat. Nos. 4,129,710, 2,784,206, and 2,784,169; German Offen No. 2,745,982; J. Appl. Polyn. Sci. 22: 2403-14 (1978); and the like.

Heretofore, some synthetic procedures for the preparation of vinylic phosphonate compounds have centered on reacting an appropriate vinylic halide with an appropriate trivalent phosphorous ester in accordance with the following reaction scheme:

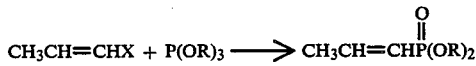

This procedure is known as the Michaeles - Arbuzov reaction. Examples of this procedure are described in "Organic Phosphorus Compounds" Vol. 7, pp. 1-486, John Wiley & Sons (1976). The Michaeles - Arbuzov reaction suffers from a number of well-known inherent defects. For example, except for the α, β-unsaturated systems, reactions involving the Michaeles - Arbuzov reaction have failed.

Similarly, reactions involving the use of transition metal salt catalysts have been used to prepare vinylic phosphonate compounds. For example, the transition metal salt catalyzed reaction of aromatic and vinylic halides with phosphites or similar trivalent phosphorus compounds to prepare the corresponding vinylic phosphonate compound is described in U.S. Pat. No. 3,493,639. This procedure also suffers from a number of defects. For example, severe reaction conditions have limited the application in industrial application.

As an alternative method, we have developed a process for the preparation of vinylic phosphonate ester compounds by isomerizing an allyl phosphonate ester into the desired vinyl phosphonate ester compound. This process is described in more detail in our copending U.S. patent application Ser. No. 627,144 entitled "BASE CATALYZED ISOMERIZATION OF ALLYL PHOSPHONATE DIESTERS TO VINYL PHOSPHONATE, DIESTERS", filed concurrently herewith and now U.S. Pat. No. 4,582,652. While this alternative process provides for excellent yields of the vinylic phosphonate ester compound it has not been totally acceptable primarily due to the lack of an acceptable commercial process for the manufacture of the allyl phosphonate ester precursor. Heretofore, pentavalent allyl phosphonate esters were prepared by either of two processes. One of these processes involves the direct reaction of an allylic halide compound with a trialkyl phosphite compound in the presence of a nickel halide catalyst at a high temperature. This process is described in detail in Japan Kokai No. 73 75, 528. The other process involves heating an allylic halide compound and a trialkyl phosphite compound in the presence of an alkyl amine in a sealed tube. This process is described in detail in Compt. Rend 259:2244 (1964). In both of these processes, conversion of the alkyl halide compound and trialkyl phosphite compound into the described product is low, and yields are not readily reproducible. These methods are obviosly not capable of commercial application for the preparation of allyl phosphonate compounds.

It is thus apparent that a need exists for an improved, practical and efficient method for the preparation of allylic phosphonate diester derivatives, which derivatives can be used as precursors in the preparation of vinyl phosphonate diester compounds.

SUMMARY OF THE INVENTION

In accordance with this invention there is provided a novel method of the preparation of allylic phosphonate compounds. More particularly, this invention provides a method for preparation of allylic phosphonate diester compounds of the formula:

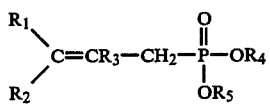

which comprises reacting an allylic compound of the formula:

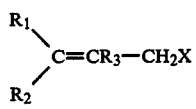

an a phosphite ester of the formula:

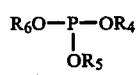

in the presence of a "catalytically effective amount" of one or more phosphinated transition metal catalysts of the formula:

[M[P(OCH$_3$)$_3$]$_5$] [B(C$_6$H$_5$)$_4$]$_2$ wherein:
X is halide or hydroxy;
M is d$^8$ transition metal;
R$_1$, R$_2$ and R$_3$ are the same or different and are hydrogen or alkyl; and
R$_4$, R$_5$ and R$_6$ are the same or different and are alkyl, cycloalkyl, aralkyl, aryl or alkaryl, either unsubstituted or substituted with one or more substituents which are inert under the reaction conditions.

The method of this invention obviates many of the disadvantages associated with the Michaeles - Arbuzov reaction, and affords a single and non-expensive method for obtaining allylic phosphonate diesters from readily available precursors in shorter reaction times, using less stringent reaction conditions in higher yields. The allylic phosphonate diesters so formed can be used as precursors in the preparation of vinylic phosphonate diester compounds, which, in turn, are precursors for compounds useful in the agricultural field.

DESCRIPTION OF THE PREFERRED EMBODIMENTS

This invention relates to a process for preparing allylic phosphonate ester compounds. Illustrative of compounds which can be prepared in accordance with the process of this invention by selection of appropriate precursors are;

0,0-dimethyl allyl phosphonate
0,0-diethyl allyl phosphonate
0,0-dipropyl allyl phosphonate
0,0-disopropyl allyl phosphonate
0,0-dibutyl allyl phosphonate
0,0-di-[tert-butyl] allyl phosphonate
0,0-di-(2,4,5-tisrchlorophenyl allyl phosphonate
2,5-dioxyphospholidine allyl oxide The process of this invention can be conveniently described by the following reaction scheme:

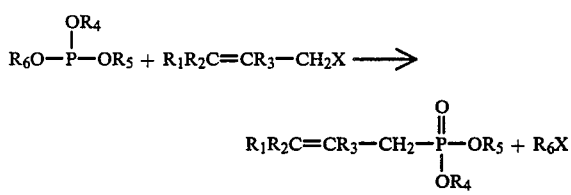

wherein R$_1$, R$_2$, R$_3$, R$_4$, R$_5$, R$_6$ and X are as described above. The process of this invention can be conveniently carried out by contacting stoichiometric amounts of the reactants or excesses thereof with a "catalytically effective amount" of one or more phosphinated transition metal compounds, either neat or in an aprotic organic solvent which is non-reactive under the process conditions. In the preferred embodiments of the invention essentially stoichiometric amounts of the reactants or excesses of no more than about 0.10 of either reactant are employed.

The phosphinated transition metal cation complexes employed as the catalysts in the process of this invention are of the formula:

[M[P(OCH$_3$)$_3$]$_5$] [B(C$_6$H$_5$)$_4$]$_2$ wherein M is as defined above. The type of transition metal cation in the catalytic complex employed can vary widely within the defined range, and include transition metals cations such as nickel (II), palladium (II), platinum (II), cobalt (II), copper (II), rhodium (III), iridium(III), gold (III), silver (I) and the like. Preferred for use in the process of this invention are complexes in which the d$^8$ transition metal cation is nickel (II), palladium (II) or platinum (II).

The d$^8$ transition metal catalysts, pentakis-(trimethylphosphite) d$^8$ - metal bis(tetraphenylborate), [M[P(OCH$_3$)$_3$]$_5$] [B(C$_6$H$_5$)$_4$]$_2$ as employed in the process of this invention can be prepared in accordance with conventional procedures. For example, these catalyst can be prepared by reacting the transition metal cation with trimethyl phosphite. The metal cation is usually complexed with a liquid which is less nucleophilic than trimethyl phosphite. The resulting pentakis-(trimethylphosphite) d$^8$ transition metal cation is then reacted with a tetraphenylborate, as for example sodium tetraphenylborate, to form the desired pentakis (trimethylphosphite) d$^8$ transition metal tetraphenylborate catalyst. This procedure is described in more detail in *Inorganic Synthesis*, 20: 76(1980), which is hereby incorporated by reference.

A "catalytically effective amount" of the pentakis-(trimethyl phosphite) d$^8$ metal bis-(tetra phenyl borate) catalyst is used. As used herein, a "catalytically effective amount" is an amount of the pentakis-(trimethyl phosphite) d$^8$ metal bis-(tetra phenyl borate) catalyst which is capable of catalyzing the reaction of the allylic halide or alcohol, and the phosphite reactant to any extent. Generally, the amount of transition metal complex catalyst employed is at least about 0.01 mole percent based on the total moles of either the halide or alcohol, or phosphite (whichever is applicable) reactant. In the preferred embodiments of the invention, the amount of the transition metal complex catalyst employed will vary from about 0.01 to about 25 mole percent, and in the particularly preferred embodiments will vary from about 0.1 to about 20 mole percent on the aforementioned basis. Amongst these particularly preferred embodiments most preferred are those embodiments in which the mole percent of transition metal complex catalyst varies from about 0.1 to about 1 mole percent on the aforementioned basis.

As was noted the reaction can be carried out neat or in an appropriate solvent. The reaction can be carried out neat when both or either of the reactants are liquid under the reaction conditions. Usually at least one of the reactants is a liquid and in the preferred embodiments of the invention the reaction is carried out neat. A reaction solvent can be used when the reactants are either a liquid or solid. Useful organic solvents which can be used as the reaction medium include those solvents which do not include any functional groups which are reactive with the reactants under the reaction conditions. Illustrative of such solvents are non-reactive alcohols such as methanol, ethanol, propanal and the like; halohydrocarbons such as carbon tetrachloride, methylene dichloride, chloroform, chlorotrifluoromethane, dichloridifluoroethane, trichlorotrifluoroethane, and the like; and aromatic solvents such as benzene, toluene, xylene and the like. Preferred organic solvents for use in the practice of this invention are alkanols having from 1 to about 8 carbon atoms. Particularly preferred reaction solvents are methanol and ethanol.

Phosphite compounds which are useful as reactants in the conduct of the process of this invention are of the formula:

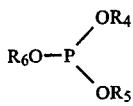

in which $R_4$, $R_5$, and $R_6$ are as described above. Illustrative of permissible $R_4$, $R_5$ and $R_6$ substitutuents are alkyl such as methyl, ethyl, isopropyl, pentyl, sec-butyl, hexyl, isobutyl, heptyl and the like; cycloalkyl such as cyclobutyl, cyclopropyl, cyclohexyl, cyclopentyl and the like; aryl such as phenyl, naphthyl and the like; alkylaryl such as 2,4-dimethylphenyl, 4-(tert - butyl)-phenyl, 3-methylphenyl and the like; and arylalkyl such as 2-phenylethyl, 3-phenylbutyl, 4-phenylbutyl, 2-phenylisopropyl and the like.

As was noted above $R_4$, $R_5$ and $R_6$ substituents may be substituted with one or more functional groups which are relatively non-reactive with the reactants, product and catalyst employed in the process under the process conditions. Illustrative of such non-reactive functional groups are halogen, i.e. fluorine, chlorine, bromine or iodine, alkoxy i.e., methoxy, ethoxy, propoxy and the like, as well as nitro, cyano, carboxy, alkoxycarbonyl, perfluoroalkyl, i.e., trifluoromethyl, and like non-reactive functional groups.

Preferred for use in the practice of this invention are phosphite compounds in which $R_4$, $R_5$ and $R_6$ are the same and are alkyl having from 1 to about 8 carbon atoms, and particularly preferred for use are compounds in which $R_4$, $R_5$ and $R_6$ are the same and are alkyl having from 1 to about 4 carbon atoms. Amongst these particularly preferred embodiments most preferred are those embodiments in which $R_4$, $R_5$ and $R_6$ are the same and are methyl or ethyl.

Phosphite compounds which can be used in the practice of this invention can be obtained from commercial sources or prepared in accordance with conventional procedures. For example, useful phosphite compounds can be conveniently prepared by reacting phosphorus trichloride with an appropriate alcohol as described in greater detail in "Organophosphorus Pesticides: Organic and Biological Chemistry" by Morhusa Eto, p. 19; CRC Press, Inc. (1979).

Allylic halide and alcohol compounds which are useful as reactants in the process of this invention are of the formula:

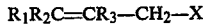

wherein X, $R_3$ and $R_4$ are as described above. Preferred for use are such compounds in which X is chloro, bromo or hydroxyl, and $R_3$ and $R_4$ are individually hydrogen, methyl or ethyl, and particularly preferred for use are such compounds in which X is chloro or bromo, and $R_3$ and $R_4$ are hydrogen. Amongst these particularly preferred compounds, allyl bromide is most preferred.

Useful allylic halide and alcohols can be obtained from commercial sources or prepared in accordance with known preparative techniques. For example, allyl halide can be prepared by reacting corresponding olefin with a halogenating agent as for example elemental halogen at elevated temperature, or N-halosuccinimide in the presence of an initiation such as ultraviolet light or a peroxide. These reactions are as described in more detail in Horner et al., *Angew Chem* 71: 349-365 (1959); Boozer and Moncrief, *J. Org. Chem.*, 27: 623 (1962): and Waling and Thaler, *J. Am. Chem. Soc.*, 83: 3877 (1961). Allyl alcohol can be prepared by reacting the corresponding allyl halide with aqueous Sodium hydroxide as described in more detail in DeWolfe and Young, *Chem. Rev.*, 56: 753-901 (1956).

The temperature employed in the process of this invention is critical and can be varied widely depending on factors known to those of skill in the art. Reaction will generally be carried out at a temperature greater than about 0° C. Temperatures within the range of from about 0° C. to about 150° C. are preferred, and reaction temperatures of from about 25° C. to about 120° C. are particularly preferred. In the most preferred embodiments of the invention, the reaction is conducted at a temperature of from about 40° C. to about 100° C.

Reaction pressures are also not critical and can be varied widely. The reaction can be carried out at superatmospheric, atmospheric and sub-atmospheric pressures. For convenience, the reaction is carried out at autogenous pressure.

The process of this invention is carried out over a period of time sufficient to produce and desired compound in adequate yield. Reaction times are influenced to a significant degree by the reaction temperature; the concentration and choice of transition metal catalyst, and the allyl and phosphite reactants; the choice and concentration of reaction solvent; and by other factors know of those skilled in the art. In general, reaction times can vary from about a few minutes to 24 hours or longer. In most instances, when employing preferred reaction conditions, reaction times will be found to vary from about 1 hour to about 2 hours.

The process of this invention can be conducted in a batch, semicontinuous or continuous fashion. The reaction can be conducted in a single reaction zone or in a plurality of reaction zones, in series or in parallel, or it may be conducted intermittently or continuously in an elongated tubular zone or series of such zones. The materials of construction employed should be inert to the reactants during the reaction and the fabrication of the equipment should be able to withstand the reaction temperatures and pressure.

The reaction zone can be fitted with one or more internal and/or external heat exchanger(s) in order to control undue temperature fluctuations, or to prevent any possible "runaway" reaction temperatures. In preferred embodiments of the process, agitation means to vary the degree of mixing of the reaction mixture can be employed. Mixing by vibration, shaking, stirring rotation, oscillation, ultrasonic vibration or the like are all illustrative of the type of agitation means contemplated. Such means are available and well known to those skilled in the art.

The reactant and catalyst may be initially introduced into th reaction zone batchwise or they may be continuously or intermittently introduced in such zone during the course of the process. Means to introduce and/or adjust the quantity of reactants introduced, either intermittently or continuously into the reaction zone during the course of the reaction can be conveniently utilized in the process especially to maintain the desired molar ratio of the reaction solvent, reactant and catalyst.

The product vinylic phosphonate diester compound can be isolated from the reaction mixture and purified employing conventional techniques. Illustrative of such techniques are evaporation, distillation, solvent extraction and recrystallization.

Compounds can be prepared in accordance with the process of this invention by selecting appropriate starting materials and reaction conditions.

The allylic phosphonate diester compounds prepared in accordance with the process of this invention have many and varied uses. For example, such compounds can be isomerized with alkali metal hydroxide compounds as for example, sodium hydroxide, to form the corresponding vinylic phosphonate diester compounds, as described in more detail in the above referenced U.S. Pat. No. 4,582,652. Such vinylic phosphonate diester compounds are useful as precusors in the preparation of plant growth regulants as described in German Offen No. 2,153,149 (1973); and of phosphatase inhibitors as described in Bartlett, et al., *Tet Letters,* 24: 2937 (1973)

The following examples are presented to more particularly illustrate the process of the invention. It will be understood, however, that although the examples may describe in detail certain preferred operating conditions of the invention, they are given primarily for purposes of illustration and the invention in the broader aspect is not limited thereto.

EXAMPLE I

Allyl bromide (12.1 g (0.1 mole)) and 12.4 g (0.1 mole) of trimethylphosphite were refluxed at 70° C. in the presence of 0.5 g ($4.7 \times 10^{-4}$ mole) of pentakis (trimethylphosphite) Nickel (II) bis(tetraphenylborate). After 1.5 hours, the product was distilled at 43°–45° C. (0.1 mm) to yield 11 g (73%) of 0,0-dimethylallylphosphonate.

EXAMPLE II

Allyl bromide (12.1 g (0.1 mole)) and 12.4 g (0.1 mole) of trimethylphosphite were refluxed at 70° C. in the presence of 0.52 g ($4.7 \times 10^{-4}$ mole) of pentakis (trimethylphosphite) palladium (II) bis(tetraphenylborate). After 1 hour, the product was distilled at 43°–45° C. (0.1 mm) to yield 11.3 g (75%) of 0,0-dimethylallylphosphonate.

EXAMPLE III

Allyl bromide (12.1 g (0.1 mole)) and 12.4 g (0.1 mole) of trimethylphosphite were refluxed at 70° C. in the presence of 0.56 g ($4.7 \times 10^{-1}$ mole) of pentakis (trimethylphosphite) platinum (II) bis(tetraphenylborate). After 1 hour, the product was distilled at 43°–45° C. (0.1 mm) to yield 10.8 g (72%) of 0,0-dimethylallylphosphonate.

EXAMPLE IV

Allyl chloride (7.6 g (0.1 mole)) and 12.4 g (0.1 mole) of trimethylphosphite were refluxed at 46° C. in the presence of 0.5 g ($4.7 \times 10^{-4}$ mole) of pentakis (trimethylphosphite) nickel (II) bis(tetraphenylborate) for 2 hours. The product was distilled at 43°–45° C. (0.1 mm) to yield 10.5 g (70%) of 0,0-dimethylallylphosphonate.

EXAMPLE V

Allyl chloride (7.6 g (0.1 mole)) and 12.4 g (0.1 mole) of trimethylphosphite were refluxed at 46° C. in the presence of 0.52 g ($4.7 \times w^{-4}$ mole) of pentakis (trimethylphosphite) palladium (II) bis(tetraphenylborate) for 2 hours. The product was distilled at 43°–45° C. (0.1 mm) to yield 10.7 g (71%) 0,0-dimethylallylphosphonate.

EXAMPLE VI

Allyl chloride (7.6 g (0.1 mole)) and 12.4 g (0.1 mole) of trimethylphosphite were refluxed at 46° C. in the presence of 0.52 g ($4.7 \times w^{-4}$ mole) of pentakis (trimethylphosphite) platinum (II) bis(tetraphenylborate) for 2 hours. The product was distilled at 43°–45° C. (0.1 mm) to yield 10.7 g (71%) 0,0-dimethylallylphosphonate.

EXAMPLE VII

Allyl alcohol (15 g (0.25 mole)) and 37 g (0.25 mole) of triemthylphosphite were refluxed at 98° C. in the presence of 0.5 g ($4.7 \times 10^{-4}$ mole) of pentakis (trimethylphosphite) nickel (II) bis(tetraphenylborate) for 1.5 hours. The product was distilled at 43°–45° C. (0.1 mm) to yield 22.3 g (60%) of 0,0-dimethylallylphosphonate.

EXAMPLE VIII

Allyl bromide (12.1 g (0.1 mole)) and 16.6 g (0.1 mole) of triethylphosphite were refluxed at 75° C. for 2 hours in the presence of 0.5 g ($4.7 \times 10^{-4}$ mole) of pentakis (trimethylphosphite) nickel (II) bis(tetraphenylborate). The product was distilled at 90°–95° C. (10 mm) to yield 14.3 g (80%) of 0,0-dietylallylphosphonate).

EXAMPLE IX

Allyl bromide (12.1 g (0.1 mole)) and 16.6 g (0.1 mole) of triethylphosphite were refluxed at 75° C. for 2 hours in the presence of 0.52 g ($4.7 \times 10^{-4}$ mole) of pentakis-(trimethylphosphite) palladium (II) bis(tetraphenylborate). The product was distilled at 90°–95° C. (10 mm) to yield 12.8 g (72%) of 0,0-diethylallylphoshonate.

EXAMPLE X

Allyl bromide (12.1 g) and 20.8 g of triisopropylphosphite were refluxed at 75° C. for 2 hours in the presence of 0.5 g ($4.7 \times 10^{-4}$ mole) of pentakis (trimethylphosphite) nickel (II) bis-(tetraphenylborate). The product was distilled at 105°–110° C. (20 mm) to yield 16 g (80%) of 0,0-diisopropylallylphosphonate.

EXAMPLE XI

Allyl bromide (12.1 g (0.1 mole)) and 25 g (0.1 mole) of tributylphosphite were refluxed at 75° C. for 2 hours in the presence of 0.5 g ($4.7 \times 10^{-4}$ mole) of pentakis (trimethylphosphite) nickel (II)-bis(tetraphenylborate). The product was distilled at 90°–95° C. (1.5 mm) to yield 18 g (77%) of 0,0-dibutylallylphosphonate.

What is claimed is:

1. A process for the preparation of an allylic phosphonate diester compounds of the formula:

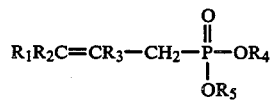

which comprises reacting an allylic compound of the formula:

and a phosphite ester of the formula:

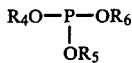

in the presence of one or more phosphonated transition metal catalyst of the formula:

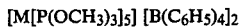

wherein:
X is halo or hydroxy;
M is a $d^8$ transition metal cation;
$R_1$, $R_2$ and $R_3$ are the same or different and are hydrogen or alkyl; and
$R_4$, $R_5$ and $R_6$ are the same or different and are alkyl, cycloalkyl, aralkyl, or alkaryl, either unsubstituted or substituted with one or more substituents which are inert under the process conditions.

2. A process according to claim 1 wherein $R_4$, $R_5$ and $R_6$ are the same.

3. A process according to claim 2 wherein $R_4$, $R_5$ and $R_6$ are unsubstituted.

4. A process according to claim 3 wherein $R_4$, $R_5$ and $R_6$ are alkyl having form 1 to about 8 carbon atoms.

5. A process according to claim 4 wherein $R_4$, $R_5$ and $R_6$ are methyl, ethyl or propyl.

6. A process according to claim 1 wherein $R_4$, $R_5$ and $R_6$ are hydrogen or alkyl having from 1 to about 4 carbon atoms.

7. A process according to claim 6 wherein $R_1$, $R_2$ and $R_3$ are the same.

8. A process according to claim 7 wherein $R_1$, $R_2$ and $R_3$ are hydrogen.

9. A process according to claim 7 wherein M is nickel (II), platinum (II) or palladium (II).

10. A process according to claim 1 wherein the amount of said catalyst is at least about 0.01 mole percent based on the total moles of the reactant present in the least amount.

11. A process according to claim 10 wherein the amount of said catalyst is from about 0.01 to about 25 mole percent.

12. A process according to claim 11 wherein the amount of said catalyst is from about 0.1 to about 20 mole percent.

13. A process according to claim 12 wherein the amount of said catalyst is from about 0.1 to about 1.0 mole percent.

14. A process according to claim 1 wherein the reaction temperature is at least about 0° C.

15. A process according to claim 14 wherein the reaction temperature is about 0° C. to about 150° C.

16. A process according to claim 15 wherein the reaction temperature is between about 45° C. and about 100° C.

17. A process according to claim 1 wherein one or both of the reactants are liquid under the reaction conditions, and said reaction is carried out neat.

18. A process according to claim 1, wherein the process is performed in a non-reactive solvent at the reflux temperature of the solvent.

19. A process according to claim 1 wherein the allylic phosphonate ester product is isolated by vacuum distillation.

* * * * *